United States Patent [19]

Ohsu et al.

[11] Patent Number: 4,769,494
[45] Date of Patent: Sep. 6, 1988

[54] PROCESS FOR PRODUCING O,O-DI-LOWER-ALKYLCHLOROTHIO-PHOSPHATE

[75] Inventors: Motomasa Ohsu, Niihama; Koichi Kamemoto, Toyonaka; Manabu Yahata; Tooru Tokumaru, both of Oita; Takeshi Hioki, Osaka; Hiroshi Ueda, Oita, all of Japan

[73] Assignee: Sumitomo Chemical Company, Limited, Osaka, Japan

[21] Appl. No.: 11,009

[22] Filed: Feb. 5, 1987

[30] Foreign Application Priority Data

Feb. 20, 1986 [JP] Japan .................................. 61-35569
Dec. 2, 1986 [JP] Japan ................................ 61-288576

[51] Int. Cl.$^4$ .............................................. C07F 9/02
[52] U.S. Cl. ...................................................... 568/14
[58] Field of Search .......................................... 568/14

[56] References Cited

U.S. PATENT DOCUMENTS

| | | | |
|---|---|---|---|
| 4,032,603 | 6/1977 | Kaschuba et al. | 568/14 XR |
| 4,371,509 | 2/1983 | Grosse | 568/14 XR |
| 4,470,933 | 9/1984 | Michalski et al. | 568/14 XR |

*Primary Examiner*—Paul F. Shaver
*Attorney, Agent, or Firm*—Stevens, Davis, Miller & Mosher

[57] ABSTRACT

A continuous process for producing O,O-di-lower alkylchlorothiophosphate very important as an intermediate for organo-phosphate series agricultural chemicals which comprises continuously reacting phosphorus sulfochloride with a lower alcohol in the presence of caustic soda according to a multi-stage reaction form comprising from 3 to 8 stages in which the following conditions are satisfied:

(1) The amounts of caustic soda and a lower alcohol used shall be from 2 to 2.2 moles and 10 moles or more, respectively, based on 1 mole of phosphorus sulfochloride.

(2) Caustic soda, water and the lower alcohol shall be used as a caustic soda/water/lower alcohol solution, and besides the caustic soda concentration of the aqueous caustic soda in said solution shall be from 30.0 to 99.5 wt.%.

(3) To the 1st reaction stage shall be continuously supplied the whole amount of phosphorus sulfochloride required and from 45 to 85 wt.% each of the amounts of caustic soda and the lower alcohol required; and to the 2nd and subsequent reaction stages shall be continuously supplied the residual caustic soda and lower alcohol in divided portions so that the substantial amounts supplied become successively small toward the final reaction stage.

(4) The temperature of the reaction system shall be $-5°$ C. or lower.

(5) The residence time in the reaction system shall be within 4 hours.

1 Claim, 1 Drawing Sheet

F I G. 1
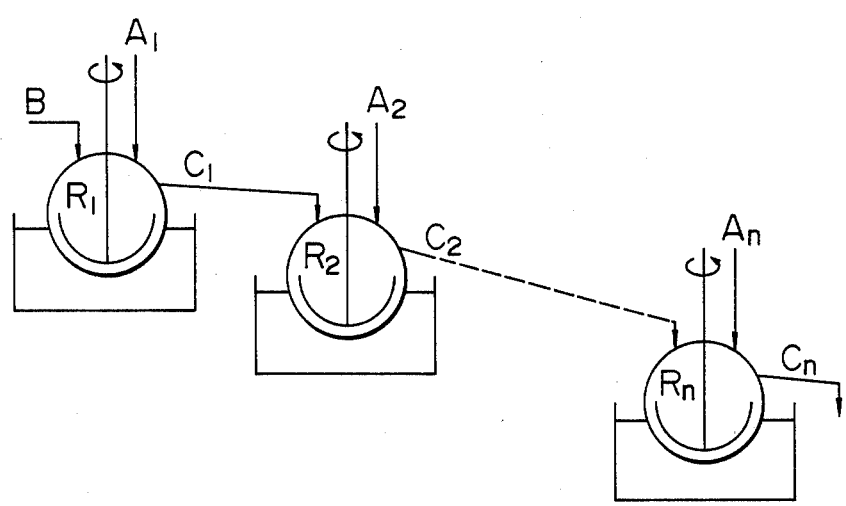

PROCESS FOR PRODUCING O,O-DI-LOWER-ALKYLCHLOROTHIOPHOSPHATE

The present invention relates to an improved continuous process for producing 0,0-di-lower-alkylchlorothiophosphate.

0,0-di-lower-alkylchlorothiophosphate is a very important compound which is widely used as an intermediate for organo-phosphate series agricultural chemicals such as 0,0-dimethyl-0-(4-nitrophenyl)thiophosphate, 0,0-dimethyl-0-(3-methyl-4-nitrophenyl)thiophosphate, 0,0-dimethyl-0-(4-cyanophenyl)thiophosphate, 0,0-dimethyl-0-(2,6-dichloro-4-methylphenyl)thiophosphate, 0,0-diethyl-0,(4-nitrophenyl)thiophosphate, etc. About its production, a process of continuously reacting phosphorus sulfochloride with sodium lower-alcoholate is well known (Japanese patent Publication No. 37654/1975).

However, as a result of an alteration in the electrolytic process which has been forwarded to avoid environmental pollution owing to the use of mercury, easy access to large quantities of sodium lower-alcholate, which is a material for this reaction, has become difficult, and therefore it is now no longer said that said well-known process is an advantageous one.

Because of this, there has been a great demand for the development of a process for producing 0,0-dilower-alkylchlorothiophosphate continuously and easily without using sodium lower-alcoholate and yet in a yield of at least the same degree as in the conventional process.

In view of this present situation, with the object of developing a continuous process for producing 0,0-di-lower-alkylchlorothiophosphate without using sodium lower-alcoholate, the present inventors studied an industrially advantageous continuous process for producing 0,0-di-lower-alkylchlorothiophosphate using cheaply and easily available caustic soda and lower alcohol as materials.

Hitherto, there is known a method of producing 0,0-di-lower-alkylchlorothiophosphate in a batch form using phosphorus sulfochloride, a lower alcohol and caustic soda. In most cases, however, this batch method usually takes a means of once producing 0-lower-alkyl-dichlorothiophosphate and then adding a caustic soda/lower alcohol solution thereto, being disadvantageous in terms of process to carry it out on a large scale in industry. Further, for continuously producing 0,0-di-lower-alkylchlorothiophosphate by this batch method in which the caustic soda/lower alcohol solution needs to be added dropwise in small portions, infinite-stage reaction vessles are required, so that this method is economically disadvantageous.

On the other hand, phosphorus sulfochloride which is a material, 0,0-di-lower-alkylchlorothiophosphate which is a product aimed at, and 0-methyldichlorothiophosphate which is an intermediate therefor, are known to be unstable to water.

Consequently, when lower-alcoholate is used as described in the foregoing Japanese Patent Publication No. 37654/1975, such problem does not occur because no water is formed by the reaction. When, however, caustic soda is used as in the present invention, water is formed by the reaction and besides an aqueous caustic soda solution is used, so that a large quantity of water is present in the system as a matter of course.

The present inventors extensively studied a process for producing the desired 0,0-di-lower-alkylchlorothiophosphate industrially advantageously under such severe conditions, and as a result, found that an efficient manufacturing method on a commercial scale cannot be established until all the conditions specified by the present invention are satisfied. The present inventors thus completed the present invention.

The present invention provides a continuous process for producing 0,0-di-lower-alkylchlorothiophosphate by continuously reacting phosphorus sulfochloride with a lower alcohol in the presence of caustic soda according to a multi-stage reaction form comprising from 3 to 8 stages characterized in that the following conditions are satisfied:

(1) The amounts of caustic soda and a lower alcohol used shall be from 2 to 2.2 moles and 10 moles or more, respectively, based on 1 mole of phosphorus sulfochloride.

(2) Caustic soda, water and the lower alcohol shall be used as a caustic soda/water/lower alcohol solution, and besides the caustic soda concentration of the aqueous caustic soda in said solution shall be from 30.0 to 99.5 wt. %. (3) To the 1st reaction stage shall be continuously supplied the whole amount of phosphorus sulfochloride required and from 45 to 85 wt. % each of the amounts of caustic soda and the lower alcohol required; and to the 2nd and subsequent reaction stages shall be continuously supplied the residual caustic soda and lower alcohol in divided portions so that the substantial amounts supplied become successively small toward the final reaction stage.

(4) The temperature of the reaction system shall be $-5°$ C. or lower.

(5) The residence time in the reaction system shall be within 4 hours.

Hereupon, "lower alcohol" referred to herein means an aliphatic alcohol having from 1 to 3 carbon atoms.

The outline of the present invention will be explained below with reference to the accompanying drawing.

FIG. 1 is a schematic view illustrating a continuous reaction apparatus comprising n reaction vessels ($3 \leq n \leq 8$). Every reaction vessel of from $R_1$ to $R_n$ is equipped with a stirrer, a caustic soda/water/lower alcohol soloution supply pipe ($A_1$ to $A_n$), an overflow pipe for the reaction solution ($C_1$ to $C_n$) and a cooling apparatus for keeping the reaction solution at a low temperature, and the 1st reaction vessel is equipped with a phosphorus sulfochloride supply pipe B.

Phosphorus sulfochloride, a material for reaction, is continuously supplied to the 1st reaction vessel through the supply pipe B. The caustic soda/water/lower alcohol solution is continuously supplied in divided portions to the reaction vessels $R_1$ to $R_n$ through the supply pipes $A_1$ to $A_n$ so that the amounts of caustic soda and the lower alcohol are in a ratio specified by the present invention. By this method, the main reaction is carried out in the 1st reaction vessel, and the reaction solution from the reaction vessels $R_1$ to $R_{n-1}$ are supplied to the respective next ones $R_2$ to $R_n$ in which reaction is furthermore promoted. Finally, the reaction solution after completion of the reaction is withdrawn from the last reaction vessel $R_n$.

In this reaction, to employ the multi-stage reaction form is very important to increase the yield of the desired product, and particularly the multi-stage reaction form comprising from 3 to 8 stages is practically very important in terms of yield and economy.

For example, in batch processes or continuous ones with only one or two stages, the yield of O,O-di-lower-alkylchlorothiophosphate is as low as at best about 75% with the formation of large quantities of impurities such as O,O-lower-alkyldichlorothiophosphate, O,O,O-tri-lower-alkylthiophosphate, etc. By increasing the number of stages, however, for example on the continuous processes with 5 or 6 stages, the yield of O,O-di-lower-alkylchlorothiophosphate can markedly be improved.

However, if the number of stages is increased for nothing, the effect corresponding to that cannot be expected only to result in that the apparatus becomes complicated to be rather disadvantageous industrially. Consequently, the number of stages is generally within eight.

Another important point of the reaction form of the present invention is the proportions of caustic soda and the lower alcohol supplied to each reaction stage. That is, to the 1st reaction stage, from 45 to 85 wt. % each, preferably from 65 to 85 wt. % each of the amounts of caustic soda and the lower alcohol required are supplied, and to the 2nd and subsequent reaction stages, the residual caustic soda and lower alcohol are supplied in divided portions so that the substantial amount added to each reaction stage becomes successively small toward the final reaction stage.

When the proportions of caustic soda and the lower alcohol supplied to the 1st reaction stage are beyond the above range, the percent decomposetion of phosphorus sulfochloride increases, and the amount of O,O,O-tri-lower-alkylthiophosphate increases to lower the yield of the desired product. Also, the amounts supplied to the 2nd and subsequent reaction stages should be successively decreased toward the final reaction stage. When the amounts supplied to the latter reaction stages are larger than those supplied to the preceding ones, the amount of O,O-tri-lower-alkylthiophosphate increases to lower the yield of the desired product.

Hereupon, "to supply so that the substantial amounts become successively small toward the final reaction stage" need not be interpreted with extreme strictness, but should be considered to mean the tendency of supply viewed from the whole. For example, it is also allowable to supply the same amount to a plural number of serial reaction stages, and to make the amount supplied to the latter reaction stages larger than that supplied to the preceding ones if a difference in amount is small. Even in the latter case, however, it is preferred to decrease the amount successively and clearly for at least the first half of the whole serial reaction stages.

Other important point of the present invention is the amounts of caustic soda and the lower alcohol based on phosphorus sulfochloride. Particularly, the amount of caustic soda used is very important, being generally from 2 to 2.2 moles, preferably from 2.05 to 2.15 moles per mole of phosphorus sulfochloride.

When the amount of caustic soda is less than 2 times by mole and also larger than 2.2 times by mole based on 1 mole of phosphorus sulfochloride, O-lower-alkyldichlorothiophosphate and O,O,O-tri-lower-alkylthiophosphate are produced respectively in large amounts to lower the yield of O,O-di-lower-alkylchlorothiophosphate.

The amount of the lower alcohol used is 10 times by mole or more, preferably 12 times by mole or more based on phosphorus sulfochloride, and its upper limit is not particularly limited from the standpoint of reaction. Generally, however, the amount is 16 times by mole, preferably 14 times by mole chiefly from the economical standpoints such as a reduction in the reaction efficiency owing to increased reaction volume and recovery of the unreacted lower alcohol. When the amount of the lower alcohol is less than 10 times by mole based on phosphorus sulfochloride, the yield of O,O-di-lower-alkylchlorothiophosphate lowers.

In the present invention, caustic soda and the lower alcohol supplied to every reaction vessel need to be supplied in the form of a caustic soda/water/lower alcohol solution, and besides, the caustic soda concentration of the aqueous caustic soda in said solution reeds to be adjusted so as to correspond to from 30.0 to 99.5 wt. %, preferably from 40.0 to 99.5 wt. %.

When the caustic soda concentration of the aqueous caustic soda is lower than 30.0 wt. %, the reaction rate becomes slow and phosphorus sulfochloride decomposes to lower the yield of the desired O,O-di-lower-alkylchlorothiophosphate.

If the lower alcohol contains water, it may be used if the caustic soda concentration calculated including that water satisfies the above range.

In preparing the caustic soda/water/lower alcohol solution, optional methods may be employed such as mixing of the lower alcohol with an aqueous caustic soda solution previously adjusted to the prescribed concentration, mixing of solid caustic soda with water and the lower alcohol or an aqueous lower alcohol solution, etc.

Generally, the caustic soda/water/lower alcohol solutions supplied to every reaction vessel have the same composition, but so far as the conditions described above are satisfied, the solutions need not have the same composition.

The most important point to the method of the present invention is to maintain the temperature of the reaction system at $-5°$ C. or lower.

In the method of the present invention, maintaining the temperature of the entire reaction system at $-5°$ C. or lower has effects of inhibiting the formation of by-products such as O,O,O-trimethylthiophosphate, etc. to increase the selectivity of O,O-di-lower-alkylchlorothiophosphate, and inhibiting the hydrolysis of phosphorus sulfochloride, O-lower-alkyldichlorothiophosphate and O,O-di-lower-alkylchlorothiophosphate which are unstable to water. Particularly, it is surprising that the foregoing effects are remarkably developed when the temperature is lowered below $-5°$ C. specified by the present invention.

Further, in the present invention, it is important to control the total of the average residence times at every reaction stage within 4 hours. The present inventors were the first to find that, from the standpoint of inhibition of hydrolysis, it is preferred to control the total of periods of time during which the above phosphorus sulfochloride and thiophosphates are brought into contact with water, i.e. average residence times at every reaction stage within 4 hours, preferably within 2 hours.

Since the reaction of the present invention is an exothermic one, heat removal becomes a problem when the average residence time is shortened. This problem, however, can be solved by mounting an external heat-exchanger on every reaction vessel.

Also, the reaction of the present invention produces sodium chloride as by-product, but if stirring is of good efficiency, the sodium chloride is dispersed in fine particles in the reaction solution, giving no adverse effect to this reaction.

By carrying out reaction operations as described above, the reaction solution from the final reaction vessel consists of two layers, one layer being an aqueous lower alcohol soluiton layer containing O,O-di-lower-alkylchlorothiophosphate, a main product, and small amounts of O-lower-alkyldichlorothiophosphate, O,O,O-tri-lower-alkylthiophosphate, etc. which are a by-product, and the other layer being one comprising partially separated O,O-di-lower-alkylchlorothiophosphate, etc. These two layers, however, turn one layer when the water content of the caustic soda/water/lower alcohol solution is lowered.

These layers are in a stage wherein fine particles have been almost uniformly dispersed, but the desired O,O-di-lower-alkylchlorothiophosphate may be separated by suitable treatment of the reaction solution. For example, the desired product can be separated by pouring the reaction solution into cold water to dissolve and remove the lower alcohol and sodium chloride, followed by dehydration and rectification of the resulting oily layers. In some cases, the separated oily layer itself may be sent to the next reaction step.

Thus, according to the method of the present invention, the desired O,O-di-lower-alkylchlorothiophosphate can be produced not only in high yields, but also economically very advantageously on industrially large scales using easily available cheap materials.

The present invention will be illustrated with reference to the following examples, but it is not limited to these examples. Parts in the examples are by weight.

EXAMPLE 1

The continuous reaction apparatus comprising 6 vessels of a form shown in FIG. 1 was used (volume ratio of from the 1st to 6th reaction vessels is 6:3:2:2:3:3, but the net volumes somewhat change depending upon the stirring rate). To the 1st reaction vessel, 337.3 parts/hour of phosphorus sulfochloride and 954.9 parts/hour of a caustic soda/water/methanol solution (caustic soda concentration, 13.6%; methanol concentration, 68.3%; water content, 18.1%) were sent usually at constant rates. To from the 2nd to 6th reaction vessels, 95.7 parts/hour, 60.7 parts/hour, 48.3 parts/hour, 18.0 parts/hour and 18.0 parts/hour, respectively, of the caustic soda/water/methanol solution were sent usually at constant rates. The molar ratios of the whole caustic soda and the whole methanol to phosphorus sulfochloride were 2.04 and 12.8, respectively. The temperatures of from the 1st to 6th reaction vessels were kept at $-15°$ C., $-20°$ C., $-20°$ C., $-17°$ C., $-16°$ C. and $-15°$ C., respectively. The total of the average residence times was 82 minutes. After the stationary state was reached, the reaction solution from the overflow pipe mounted on the 6th reaction vessel was sampled for 15 minutes, and to this solution was added 350 parts of cold water. The separated oily layer and an organic layer obtained by extracting the separated aqueous layer with toluene were dried over calcium chloride and analyzed by gas chromatography to find that: O,O-dimethylchlorothiophosphate, 73.1 parts (yield, 91.5%); O-methyldichlorothiophosphate, 0.82 part (yield, 1.0%); and O,O,O-trimethylthiophosphate, 3.7 parts (yield, 5.0%). The phosphorus analysis of the aqueous layer showed that 1.2 parts of phosphorus, as converted to PO$_4$, was contained in the aqueous layer, the percent decomposition being 2.5%.

EXAMPLE 2

The same reaction apparatus and caustic soda/water/methanol solution as used in Example 1 were used. To the 1st reaction vessel, 338.3 parts/hour of phosphorus sulfochloride and 661.8 parts/hour of the caustic soda/water/methanol solution were sent usually at constant rates. To from the 2nd to 6th reaction vessels, 302.5 parts/hour, 140.6 parts/hour, 70.3 parts/hour, 15.4 parts/hour and 15.7 parts/hour, respectively, of the caustic soda/water/methanol solution were sent usually at constant rates. The molar ratios of the whole caustic soda and the whole methanol to phosphorus sulfochloride were 2.05 and 12.9, respectively. The temperatures of from the 1st to 6th reaction vessels were kept at $-20°$ C., $-20°$ C., $-20°$ C., $-20°$ C., $-18°$ C. and $-15°$ C., respectively. The total of the average residence times was 72 minutes. After the stationary state was reached, the reaction solution from the overflow pipe mounted on the 6th reaction vessel was sampled for 15 minutes and treated and analyzed in the same manner as in Example 1 to find that: O,O-dimethylchlorothiophosphate, 72.2 parts (yield, 90.1%); O-methyldichlorothiophosphate, 0.82 part (yield, 1.0%); and O,O,O-trimethylthiophosphate, 4.2 parts (yield, 5.6%). The phosphorus analysis of the aqueous layer showed that 1.6 parts of phosphorus, as converted to PO$_4$, was contained in the aqueous layer, the percent decomposition being 3.4%.

EXAMPLE 3

The continuous reaction apparatus comprising 5 vessels of a form shown in FIG. 1 was used (volume ratio of from the 1st to 5th reaction vessels is 6:2:2:3:3, but the net volumes somewhat change depending upon the stirring rate). To the 1st reaction vessel, 337.7 parts/hour of phosphorus sulfochloride and 983.6 parts/hour of a caustic soda/water/methanol solution (caustic soda concentration, 13.7%; methanol concentration, 72.1%; water content, 14.2%) were sent usually at constant rates. To from the 2nd to 5th reaction vessels, 143.4 parts/hour, 71.9 parts/hour, 15.3 parts/hour and 15.2 parts/hour, respectively, of the caustic soda/water/methanol solution were sent usually at constant rates. The molar ratios of the whole caustic soda and the whole methanol to phosphorus sulfochloride were 2.11 and 13.9, respectively. The temperatures of from the 1st to 5th reaction vessels were kept at $-20°$ C., $-21°$ C., $-21°$ C., $-22°$ C. and $-14°$ C., respectively. The total of the average residence times was 60 minutes. Thereafter, after-treatment and analysis were carried out in the same manner as in Example 1 to find that: O,O-dimethylchlorothiophosphate, 72.1 parts (yield, 90.1%); O-methyldichlorothiophosphate, 0.82 part (yield, 1.0%); and O,O,O-trimethylthiophosphate, 4.8 parts (yield, 6.4%). The phosphorus analysis of the aqueous layer showed that 1.2 parts of phosphorus, as converted to PO$_4$, was contained in the aqueous layer, the percent decomposition being 2.5%.

EXAMPLE 4

The continuous reaction apparatus comprising 6 vessels of a form shown in FIG. 1 was used (volume ratio of from the 1st to 6th reaction vessels is 6:3:2:2:3:3, but the net volumes somewhat change depending upon the stirring rate). To the 1st reaction vessel, 337.3 parts/hour of phosphorus sulfochloride and 789.0 parts/hour of a caustic soda/water/methanol solution (caustic soda concentration, 16.51%; methanol concentration, 83.16%, water content, 0.33%) were sent usually at constant rates. To from the 2nd to 6th reaction vessels, 79.0 parts/hour, 49.4 parts/hour, 40.5 parts/hour, 14.8 parts/hour and 14.8 parts/hour, respectively, of the caustic soda/water/methanol solution were sent usually at constant rates. The molar ratios of the whole caustic soda and the whole methanol to phosphorus sulfochloride were 2.05 and 12.9, respectively. The temperatures of from the 1st to 6th reaction vessels were kept at −21° C., −21° C., −21° C., −24° C., −14° C. and −14° C., respectively. The total of the average residence times was 77 minutes. After the stationary state was reached, the reaction soluiton from the overflow pipe mounted on the 6th reaction vessel was sampled for 15 minutes and treated and analyzed in the same manrer as in Example 1 to find that: O,O-dimethylchlorothiophosphate, 74.6 parts (yield, 93.3%); O-methyldichlcrothiophosphate, 0.82 part (yield, 1.0%); and O,O,O-trimethylthiophosphate, 3.0 parts (yield, 4.0%). The phosphorus analysis of the aqueous layer showed that 0.80 part of phosphorus, as converted to PO4, was contained in the aqueous layer, the percent decomposition being 1.7%.

EXAMPLE 5

The continuous reaction apparatus comprising 5 vessels of a form shown in FIG. 1 was used (volume ratio of from the 1st to 5th reaction vessels is 6:2:2:3:3, but the net volumes somewhat change depending upon the stirring rate). To the 1st reaction vessel, 337.7 parts/hour of phosphorus sulfochloride and 789.0 parts/hour of a caustic soda/water/methanol solution (caustic soda concentration, 16.51%; methanol concentration, 83.10%; water content, 0.33%) were sent usually at constant rates. To from the 2nd to 5th reaction vessels, 114.5 parts/hour, 58.3 parts/hour, 12.8 parts/hour and 12.8 parts/hour, respectively, of the caustic soda/water/methanol solution were sent usually at constant rates. The molar ratios of the whole caustic soda and the whole methanol to phosphorus sulfochloride were 2.04 and 12.9, respectively. The temperatures of from the 1st to 5th reaction vessels were kept at −21° C., −21° C., −21° C., −24° C. and −14° C., respectively. The total of the average residence times was 65 minutes. After the stationary state was reached, the reaction solution from the overflow pipe mounted on the 5th reaction vessel was sampled for 15 minutes and treated and analyzed in the same manner as in Example 1 to find that: O,O-dimethylchlorothiophosphate, 74.0 parts (yield, 92.5%); O-methyldichlorothiophosphate, 0.82 part (yield, 1.0%); and O,O,O-trimethylthiophosphate, 3.8 parts (yield, 5.1%). The phosphorus analysis of the aqueous layer showed that 0.66 part of phosphorus, as converted to PO4, was contained in the aqueous layer, the percent decomposition being 1.4%.

EXAMPLE 6

The same reaction apparatus and caustic soda/water/methanol solution as used in Example 1 were used. To the 1st reaction vessel, 338.3 parts/hour of phosphorus sulfochloride and 649.0 parts/hour of the caustic soda/water/methanol solution were sent usually at constant rates. To from the 2nd to 6th reaction vessels, 148.5 parts/hour, 116.6 parts/hour, 57.8 parts/hour, 13.0 parts/hour and 13.0 parts/hour, respectively, of the caustic soda/water/methanol solution were sent usually at constant rates. The molar ratios of the whole caustic soda and the whole methanol to phosphorus sulfochloride were 2.06 and 13.0, respectively. The temperatures of from the 1st to 6th reaction vessels were kept at −20° C., −20° C., −20° C., −20° C., −18° C. and −15° C., respectively. The total of the average residence times was 72 minutes. After the stationary state was reached, the reaction solution from the overflow pipe mounted on the 6th reaction vessel was sampled for 15 minutes and treated and analyzed in the same manner as in Example 1 to find that: O,O-dimethylchlorothiophosphate, 74.0 parts (yield, 92.3%); O-methyldichlorothiophosphate, 0.82 part (yield, 1.0%); and O,O,O-trimethylthiphosphate, 3.7 parts (yield, 5.0%). The phosphorus analysis of the aqueous layer showed that 1.3 parts of phosphorus, as converted to PO4, was contained in the aqueous layer, the percent decomposition being 2.7%.

EXAMPLES 7 TO 9

Procedure was carried out in the same manner as in Example 5 except that the temperatures of from the 1st to 5th reaction vessels were changed as shown in Table 1.

TABLE 1

| | Operation condition [Reaction temperature (°C.)] [Residence time (min)] | | | | | | | Yield (%) | |
|---|---|---|---|---|---|---|---|---|---|
| Example No. | 1st vessel | 2nd vessel | 3rd vessel | 4th vessel | 5th vessel | MMCT | DMCT | TRI | percent decpmposition |
| 7 | $\frac{-16}{24.4}$ | $\frac{-19}{8.1}$ | $\frac{-17}{8.1}$ | $\frac{-15}{12.2}$ | $\frac{-14}{12.2}$ | 1.0 | 92.0 | 5.2 | 1.8 |
| 8 | $\frac{-12}{24.4}$ | $\frac{-15}{8.1}$ | $\frac{-13}{8.1}$ | $\frac{-12}{12.2}$ | $\frac{-11}{12.2}$ | 1.0 | 91.0 | 5.5 | 2.4 |
| 9 | $\frac{-6}{24.4}$ | $\frac{-6}{8.1}$ | $\frac{-7}{8.1}$ | $\frac{-6}{12.2}$ | $\frac{-7}{12.2}$ | 1.0 | 90.0 | 6.0 | 3.0 |

MMCT: O—methyldichlorothiophosphate
DMCT: O,O—dimethylchlorothiophosphate
TRI: O,O,O—trimethylthiophosphate

EXAMPLE 10

The continuous reaction apparatus comprising 5 vessels of a form shown in FIG. 1 was used (volume ratio of from the 1st to 5th reaction vessels is 6:2:2:3:3, but the net volumes somewhat change depending upon the stirring rate). To the 1st reaction vessel, 337.7 parts/hour of phosphorus sulfochloride and 933.7 parts/hour of a caustic soda/water/methanol solution (caustic soda concentration, 14.0%; methanol concentration, 74.5%; water content, 11.5%) were sent usually at constant rates. To from the 2nd to 5th reaction vessels, 137.3 parts/hour, 68.1 parts/hour, 15.3 parts/hour and 15.3 parts/hour, respectively, of the caustic soda/water/methanol solution were sent usually at constant rates. The molar ratios of the whole caustic soda and the whole methanol to phosphorus sulfochloride were 2.05 and 13.6, respectively. The temperatures of from the 1st to 5th reaction vessels were kept at −20° C., −21° C., −21° C., −22° C. and −14° C., respectively. The total of the average residence times was 60 minutes. Thereafter, after-treatment and analysis were carried out in the same manner as in Example 1 to find that: O,O-dimethylchlorothiophosphate, 73.0 parts (yield, 91.2%); O-methyldichlorothiophosphate, 0.82 part (yield, 1.0%); and O,O,O-trimethylthiophosphate, 4.2 parts (yield, 5.6%). The phosphorus analysis of the aqueous layer showed that 1.0 part of phosphorus, as converted to $PO_4$, was contained in the aqueous layer, the percent decomposition being 2.2%.

EXAMPLE 11

The same reaction apparatus and caustic soda/water/methanol solution as used in Example 4 were used. To the 1st reaction vessel, 338.3 parts/hour of phosphorus sulfochloride and 449.3 parts/hour of the caustic soda/water/methanol solution were sent usually at constant rates. To from the 2nd to 6th reaction vessels, 291.3 parts/hour, 164.9 parts/hour, 57.3 parts/hour, 12.8 parts/hour and 12.8 parts/hour, respectively, of the caustic soda/water/methanol solution were sent usually at constant rates. The molar ratios of the whole caustic soda and the whole methanol to phosphorus sulfochloride were 2.06 and 12.9, respectively. The temperatures of from the 1st to 6the reaction vessels were kept at −20° C., −20° C., −20° C., −20° C., −18° C. and −15° C., respectively. The total of the average residence times was 72 minutes. After the stationary state was reached, the reaction solution from the overflow pipe mounted on the 6th reaction vessel was sampled for 15 minutes and treated and analyzed in the same manner as in Example 1 to find that: O,O-dimethylchlorothiophosphate, 71.3 parts (yield, 89.0%); O-methyldichlorothiophosphate, 0.82 part (yield, 1.0%); and O,O,O-trimethylthiophosphate, 4.27 parts (yield, 5.7%). The phosphorus analysis of the aqueous layer showed that 2.0 parts of phosphorus, as converted to $PO_4$, was contained in the aqueous layer, the percent decomposition being 4.3%.

EXAMPLE 12

The continuous reaction apparatus comprising 6 vessels of a form shown in FIG. 1 was used (volume ratio of from the 1st to 6th reaction vessels is 6:3:2:2:3:3, but the net volumes somewhat change depending upon the stirring rate). To the 1st reaction vessel 337.3 parts/hour of phosphorus sulfochloride and 954.9 parts/hour of a caustic soda/water/methanol solution (caustic soda concentration, 13.6%; methanol concentration, 68.3%; water content, 18.1%) were sent usually at constant rates. To from the 2nd to 6th reaction vessels, 95.7 parts/hour, 60.7 parts/hour, 48.3 parts/hour, 18.0 parts/hour ard 18.0 parts/hour, respectively, of the caustic soda/water/methanol solution were sent usually at constant rates. The molar ratios of the whole caustic soda and the whole methanol to phosphorus sulfochloride were 2.04 and 12.8, respectively. The temperatures of from the 1st to 6th reaction vessels were kept at −10° C., −9° C., −10° C., −11° C., −9° C. and −9° C., respectively. The total of the average residence times was 82 minutes. After the stationary state was reached, the reaction solution from the overflow pipe mounted on the 6th reaction vessel was sampled for 15 minutes, treated in the same manner as in Example 1 and analyzed by gas chromatography to find that: O,O-dimethylchlorothiophosphate, 71.9 parts (yield, 90.0%); O-methyldichlorothiophosphate, 0.82 part (yield, 1.0%); and O,O,O-trimethylthiophosphate, 4.5 parts (yield, 6.0%). The phosphorus analysis of the aqueous layer showed that 1.4 parts of phosphorus, as converted to $PO_4$, was contained in the aqueous layer, the percent decomposition being 3.0%.

EXAMPLE 13

The continuous reaction apparatus comprising 5 vessels of a form shown in FIG. 1 was used (volume ratio of from the 1st to 5th reaction vessels is 6:2:2:3:3, but the net volumes somewhat change depending upon the stirring rate). To the 1st reaction vessel, 337.7 parts/hour of phosphorus sulfochloride and 1077.8 parts/hour of a caustic/water/ethanol solution (caustic soda concentration, 12.06%; ethanol concentration, 87.69%; water content, 0.25%) were sent usually at constant rates. To from the 2nd to 5th reaction vessels, 156.5 parts/hour, 79.6 parts/hour, 17.5 parts/hour and 17.5 parts/hour, respectively, of the caustic soda/water/ethanol solution were sent usually at constant rates. The molar ratios of the whole caustic soda and the whole ethanol to phosphorus sulfochloride were 2.04 and 12.9, respectively. The temperatures of from the 1st to 5th reaction vessels were kept at −16° C., −19° C., −17° C., −15° C. and −14° C., respectively. The total of the average residence times was 77.9 minutes. After the stationary state was reached, the reaction solution from the overflow pipe mounted on the 5th reaction vessel was sampled for 15 minutes and treated and analyzed in the same manner as in Example 1 to find that: O,O-diethylchlorothiophosphate, 86.0 parts (yield, 91.5%); O-ethyldichlorothiophosphate, 0.89 part (yield, 1.0%); and O,O,O-triethylthiophosphate, 5.3 parts (yield, 5.5%). The phosphorus analysis of the aqueous layer showed that 0.95 part of phosphorus, as converted to $PO_4$, was contained in the aqueous layer, the percent decomposition being 2.0%.

EXAMPLE 14

The continuous reaction apparatus comprising 6 vessels of a form shown in FIG. 1 was used (volume ratio of from the 1st to 6th reaction vessels is 6:3:2:2:3:3, but the net volumes somewhat change depending upon the stirring rate). To the 1st reaction vessel, 337.3 parts/hour of phosphorus sulfochloride and 1248.1 parts/hour of a caustic soda/water/ethanol solution (caustic soda concentration, 10.45%; ethanol concentration, 75.63%; water content, 13.91%) were sent usually at constant rates. To from the 2nd to 6th reaction vessels, 125.0 parts/hour, 78.1 parts/hour, 64.0 parts/hour, 23.4 parts/hour and 23.4 parts/hour, respectively, of the caustic soda/water/ethanol solution were sent usually at constant rates. The molar ratios of the whole caustic soda and the whole ethanol to phosphorus sulfochloride were 2.05 and 12.9, respectively. The temperatures of from the 1st to 6th reaction vessels were kept at −15° C., −20° C., −20° C., −17° C., −16° C. and −15° C., respectively. The total of the average residence times was 98.2 minutes. After the stationary state was reached, the reaction solution from the overflow pipe mounted on the 6th reaction vessel was sampled for 15 minutes, treated in the same manner as in Example 1 and analyzed by gas chromatography to find that: O,O-diethylchlorothiophosphate, 84.9 parts (yield, 90.5%); O- ethyldichlorothiophosphate, 0.89 part (yield, 1.0%); and O,O,O-triethylthiophosphate, 5.5 parts (yield, 5.8%). The phosphorus analysis of the aqueous layer showed that 1.3 parts of phosphorus, as converted to $PO_4$, was contained in the aqueous layer, the percent decomposition being 2.7%.

EXAMPLE 15

The continuous reaction apparatus comprising 5 vessels of a form shown in FIG. 1 was used (volume ratio of from the 1st to 5th reaction vessels is 6:2:2:3:3, but the net volumes somewhat change depending upon the stirring rate). To the 1st reaction vessel, 337.7 parts/hour of phosphorus sulfochloride and 1365.4 parts/hour of a caustic soda/water/isopropanol solution (caustic soda concentration, 9.52%; isopropanol concentration, 90.28%; water content, 0.20%) were sent usually at constant rates. To from the 2nd to 5th reaction vessels, 198.2 parts/hour, 100.8 parts/hour, 22.2 parts/hour and 22.2 parts/hour, respectively, of the caustic soda/water/isopropanol solution were sent usually at constant rates. The molar ratios of the whole caustic soda and the whole isopropanol to phosphorus sulfochloride were 2.04 and 12.9, respectively. The temperatures of from the 1st to 5th reaction vessels were kept at $-15°$ C., $-18°$ C., $-16°$ C., $-15°$ C. and $-14°$ C., respectively. The total of the average residence times was 77.9 minutes. After the stationary state was reached, the reaction solution from the overflow pipe mounted on the 5th reaction vessel was sampled for 15 minutes and treated and analyzed in the same manner as in Example 1 to find that: O,O-diisopropylchlorothiophosphate, 99.1 parts (yield, 91.8%); O-isopropyldichlorothiophosphate, 0.96 part (yield, 1.0%); and O,O,O-triisopropylthiophosphate, 5.9 parts (yield, 5.1%). The phosphorus analysis of the aqueous layer showed that 0.99 part of phosphorus, as converted to $PO_4$, was contained in the aqueous layer, the percent decomposition being 2.1%.

EXAMPLE 16

The continuous reaction apparatus comprising 6 vessels of a form shown in FIG. 1 was used (volume ratio of from the 1st to 6th reaction vessels is 6:3:2:2:3:3, but the net volumes somewhat change depending upon the stirring rate). To the 1st reaction vessel, 337.3 parts/hour of phosphorus sulfochloride and 1524.4 parts/hour of a caustic soda/water/isopropanol solution (caustic soda concentration, 8.52%, isopropanol concentration, 80.15%; water content, 11.34%) were sent usually at constant rates. To from the 2nd to 6th reaction vessels, 152.6 parts/hour, 95.4 parts/hour, 78.2 parts/hour, 28.6 parts/hour and 28.6 parts/hour, respectively, of the caustic soda/water/isopropanol solution were sent usually at constant rates. The molar ratios of the whole caustic soda and the whole isopropanol to phosphorus sulfochloride were 2.04 and 12.8, respectively. The temperatures of from the 1st to 6th reaction vessels were kept at $-15°$ C., $-20°$ C., $-20°$ C., $-17°$ C., $-16°$ C. and $-15°$ C., respectively. The total of the average residence times was 98.2 minutes. After the stationary state was reached, the reaction solution from the overflow pipe mounted on the 6th reaction vessel was sampled for 15 minutes and treated and analyzed in the same manner as in Example 1 to find that: O,O-diisopropylchlorothiphosphate, 97.8 parts (yield, 90.8%); O-isopropyldichlorothiophosphate, 0.96 part (yield, 1.0%); and O,O,O-triisopropylthiophosphate, 6.5 parts (yield, 5.6%). The phosphorus analysis of the aqueous layer showed that 1.2 parts of phosphorus, as converted to $PO_4$, was contained in the aqueous layer, the percent decomposition being 2.6%.

The results of Examples 1 to 16 will be collectively shown in Tables 2, 3 and 4.

COMPARATIVE EXAMPLES 1 TO 10

Reaction was carried out under the conditions shown in Table 5 using the continuous reaction apparatus of a form shown in FIG. 1.

BRIEF EXPLANATION OF THE DRAWINGS

FIG. 1 shows a continuous reaction apparatus for practicing the present invention in the form of flow sheet.

In the figure, $R_1$ to $R_n$ represent reaction vessels, B represents a phosphorus sulfochloride supply pipes, $A_1$ to $A_n$ represent caustic soda/water/lower alcohol solution supply pipe, $C_1$ to $C_n$ represent overflow pipes and n represents an integer of from 3 to 8.

TABLE 2

(Examples 1 to 12)

| | Operation condition | | | | | | | | | | | | | |
|---|---|---|---|---|---|---|---|---|---|---|---|---|---|---|
| | Reaction temperature (°C.) Residence time (min) | | | | | | Ratio of caustic soda/water/methanol solutions fed (%) | | | | | | Molar ratio | |
| Example | 1st vessel | 2nd vessel | 3rd vessel | 4th vessel | 5th vessel | 6th vessel | 1st vessel | 2nd vessel | 3rd vessel | 4th vessel | 5th vessel | 6th vessel | $\frac{NaOH}{PSCl_3}$ | $\frac{CH_3OH}{PSCl_3}$ |
| 1 | $\frac{-15}{25.9}$ | $\frac{-20}{12.9}$ | $\frac{-20}{8.6}$ | $\frac{-17}{8.6}$ | $\frac{-16}{12.9}$ | $\frac{-15}{12.9}$ | 79.8 | 8.0 | 5.1 | 4.0 | 1.5 | 1.5 | 2.04 | 12.8 |
| 2 | $\frac{-20}{22.7}$ | $\frac{-20}{11.4}$ | $\frac{-20}{7.6}$ | $\frac{-20}{7.6}$ | $\frac{-18}{11.4}$ | $\frac{-15}{11.4}$ | 54.8 | 25.1 | 11.7 | 5.8 | 1.3 | 1.3 | 2.06 | 12.9 |
| 3 | $\frac{-20}{22.5}$ | $\frac{-21}{7.5}$ | $\frac{-21}{7.5}$ | $\frac{-22}{11.3}$ | $\frac{-14}{11.3}$ | | 80.0 | 11.7 | 5.8 | 1.2 | 1.2 | | 2.11 | 13.9 |
| 4 | $\frac{-21}{24.3}$ | $\frac{-21}{12.2}$ | $\frac{-21}{8.1}$ | $\frac{-24}{8.1}$ | $\frac{-14}{12.2}$ | $\frac{-14}{12.2}$ | 79.9 | 8.0 | 5.0 | 4.1 | 1.5 | 1.5 | 2.05 | 12.9 |
| 5 | $\frac{-21}{24.4}$ | $\frac{-21}{8.1}$ | $\frac{-21}{8.1}$ | $\frac{-24}{12.2}$ | $\frac{-24}{12.2}$ | | 79.9 | 11.6 | 5.9 | 1.3 | 1.3 | | 2.04 | 12.9 |
| 6 | $\frac{-20}{22.7}$ | $\frac{-20}{11.4}$ | $\frac{-20}{7.6}$ | $\frac{-20}{7.6}$ | $\frac{-18}{11.4}$ | $\frac{-15}{11.4}$ | 65.0 | 14.9 | 11.7 | 5.8 | 1.3 | 1.3 | 2.06 | 13.0 |
| 7 | $\frac{-16}{24.4}$ | $\frac{-19}{8.1}$ | $\frac{-17}{8.1}$ | $\frac{-15}{12.2}$ | $\frac{-14}{12.2}$ | | 79.9 | 11.6 | 5.9 | 1.3 | 1.3 | | 2.04 | 12.9 |

TABLE 2-continued
(Examples 1 to 12)

| Example | 1st vessel | 2nd vessel | 3rd vessel | 4th vessel | 5th vessel | 6th vessel | 1st vessel | 2nd vessel | 3rd vessel | 4th vessel | 5th vessel | 6th vessel | NaOH/PSCl3 | CH3OH/PSCl3 |
|---|---|---|---|---|---|---|---|---|---|---|---|---|---|---|
| 8 | $\frac{-12}{24.4}$ | $\frac{-15}{8.1}$ | $\frac{-13}{8.1}$ | $\frac{-12}{12.2}$ | $\frac{-11}{12.2}$ | | 79.9 | 11.6 | 5.9 | 1.3 | 1.3 | | 2.04 | 12.9 |
| 9 | $\frac{-6}{24.4}$ | $\frac{-6}{8.1}$ | $\frac{-7}{8.1}$ | $\frac{-6}{12.2}$ | $\frac{-7}{12.2}$ | | 79.9 | 11.6 | 5.9 | 1.3 | 1.3 | | 2.04 | 12.9 |
| 10 | $\frac{-20}{22.5}$ | $\frac{-21}{7.5}$ | $\frac{-21}{7.5}$ | $\frac{-22}{11.3}$ | $\frac{-14}{11.3}$ | | 79.8 | 11.7 | 5.8 | 1.3 | 1.3 | | 2.05 | 13.6 |
| 11 | $\frac{-20}{22.7}$ | $\frac{-20}{11.1}$ | $\frac{-20}{7.6}$ | $\frac{-20}{7.6}$ | $\frac{-18}{11.4}$ | $\frac{-15}{11.4}$ | 45.5 | 45.5 | 16.7 | 5.8 | 1.3 | 1.3 | 2.04 | 12.8 |
| 12 | $\frac{-10}{25.9}$ | $\frac{-9}{12.9}$ | $\frac{-10}{8.6}$ | $\frac{-11}{8.6}$ | $\frac{-9}{12.9}$ | $\frac{-9}{12.9}$ | 79.8 | 8.0 | 5.1 | 4.0 | 1.5 | 1.5 | 2.04 | 12.8 |

| Example | Concentrations of caustic soda/water/methanol solution (wt. %) NaOH | H2O | CH3OH | Yield (%) MMCT | DMCT | TRI | Decomposition | Remark |
|---|---|---|---|---|---|---|---|---|
| 1 | 13.6 | 18.1 | 68.3 | 1.0 | 91.5 | 5.0 | 2.5 | Concentration of aqueous caustic soda, 42.9% |
| 2 | 13.6 | 18.1 | 68.3 | 1.2 | 90.1 | 5.6 | 3.4 | Concentration of aqueous caustic soda, 42.9% |
| 3 | 13.7 | 14.2 | 72.1 | 1.0 | 90.1 | 6.4 | 2.5 | Concentration of aqueous caustic soda, 49.1% |
| 4 | 16.51 | 0.33 | 83.16 | 1.0 | 93.3 | 4.0 | 1.7 | Concentration of caustic soda, 98.0% |
| 5 | 16.51 | 0.33 | 83.16 | 1.0 | 92.5 | 5.1 | 1.4 | Concentration of caustic soda, 98.0% |
| 6 | 16.51 | 0.33 | 83.16 | 1.0 | 92.3 | 5.0 | 2.7 | Concentration of caustic soda, 98.0% |
| 7 | 16.51 | 0.33 | 83.16 | 1.0 | 92.0 | 5.2 | 1.8 | Concentration of caustic soda, 98.0% |
| 8 | 16.51 | 0.33 | 83.16 | 1.0 | 91.1 | 5.5 | 2.4 | Concentration of caustic soda, 98.0% |
| 9 | 16.51 | 0.33 | 83.16 | 1.0 | 90.0 | 6.0 | 3.0 | Concentration of caustic soda, 98.0% |
| 10 | 14.0 | 11.5 | 74.5 | 1.0 | 91.2 | 5.6 | 2.2 | Concentration of aqueous caustic soda, 54.9% |
| 11 | 16.51 | 0.33 | 83.16 | 1.0 | 89.0 | 5.7 | 4.3 | Concentration of caustic soda, 98.0% |
| 12 | 13.6 | 18.1 | 68.36 | 1.0 | 90.0 | 6.0 | 3.0 | Concentration of aqueous caustic soda, 42.9% |

MMCT: O—methyldichlorothiophosphate
DMCT: O,O—dimethylchlorothiophosphate
TRI: O,O,O—trimethylthiophosphate

TABLE 3
(Examples 13 and 14)

Operation condition

| Example | Reaction temperature (°C.) / Residence time (min) 1st vessel | 2nd vessel | 3rd vessel | 4th vessel | 5th vessel | 6th vessel | Ratio of caustic soda/water/ethanol solutions fed (%) 1st vessel | 2nd vessel | 3rd vessel | 4th vessel | 5th vessel | 6th vessel | Molar ratio NaOH/PSCl3 | C2H5OH/PSCl3 |
|---|---|---|---|---|---|---|---|---|---|---|---|---|---|---|
| 13 | $\frac{-16}{29.3}$ | $\frac{-19}{9.79}$ | $\frac{-17}{9.7}$ | $\frac{-15}{14.6}$ | $\frac{-14}{14.6}$ | | 79.9 | 11.6 | 5.9 | 1.3 | 1.3 | | 2.04 | 12.9 |
| 14 | $\frac{-15}{31.1}$ | $\frac{-20}{15.5}$ | $\frac{-20}{10.3}$ | $\frac{-17}{10.3}$ | $\frac{-16}{15.5}$ | $\frac{-15}{15.5}$ | 79.9 | 8.0 | 5.0 | 4.1 | 1.5 | 1.5 | 2.05 | 12.9 |

| Example | Concentration of caustic soda/water/ethanol solution (wt. %) NaOH | H2O | C2H5OH | Yield (%) MECT | DECT | ETRI | Decomposition | Remark |
|---|---|---|---|---|---|---|---|---|
| 13 | 12.06 | 0.25 | 87.69 | 1.0 | 91.5 | 5.5 | 2.0 | Concentration of caustic soda, 98.0% |
| 14 | 10.45 | 13.91 | 75.63 | 1.0 | 90.5 | 5.8 | 2.7 | Concentration of aqueous caustic soda, 42.9% |

MECT: O—ethyldichlorothiophosphate
DECT: O,O—diethylchlorothiophosphate
ETRI: O,O,O—triethylthiophosphate

TABLE 4
(Examples 15 and 16)

Operation condition

| Example | Reaction temperature (°C.) / Residence time (min) 1st vessel | 2nd vessel | 3rd vessel | 4th vessel | 5th vessel | 6th vessel | Ratio of caustic soda/water/isopropanol solutions fed (%) 1st vessel | 2nd vessel | 3rd vessel | 4th vessel | 5th vessel | 6th vessel | Molar ratio NaOH/PSCl3 | C3H7OH/PSCl3 |
|---|---|---|---|---|---|---|---|---|---|---|---|---|---|---|
| 15 | $\frac{-15}{29.3}$ | $\frac{-18}{9.7}$ | $\frac{-16}{9.7}$ | $\frac{-15}{14.6}$ | $\frac{-14}{14.6}$ | | 79.9 | 11.6 | 5.9 | 1.3 | 1.3 | | 2.04 | 12.9 |
| 16 | $\frac{-15}{31.1}$ | $\frac{-20}{15.5}$ | $\frac{-20}{10.3}$ | $\frac{-17}{10.3}$ | $\frac{-16}{15.5}$ | $\frac{-15}{15.5}$ | 79.9 | 8.0 | 5.0 | 4.1 | 1.5 | 1.5 | 2.04 | 12.8 |

Concentration of caustic soda/water/isopropanol

TABLE 4-continued (Examples 15 and 16)

| Example | solution (wt. %) NaOH | solution (wt. %) H₂O | solution (wt. %) C₃H₇OH | Yield (%) MPCT | Yield (%) DPCT | Yield (%) PTRI | Decomposition | Remark |
|---|---|---|---|---|---|---|---|---|
| 15 | 9.52 | 0.20 | 90.28 | 1.0 | 91.8 | 5.1 | 2.1 | Concentration of caustic soda, 98.0% |
| 16 | 8.52 | 11.34 | 80.15 | 1.0 | 90.8 | 5.6 | 2.6 | Concentration of aqueous caustic soda, 42.9% |

MPCT: O—isopropyldichlorothiophosphate
DPCT: O,O—diisopropylchlorothiophosphate
PTRI: O,O,O—triisoproplthiophosphate

TABLE 5

(Comparative examples 1 to 10)

| Comparative Example | Reaction temperature (°C.) / Residence time (min) 1st vessel | 2nd vessel | 3rd vessel | 4th vessel | 5th vessel | 6th vessel | Ratio of caustic soda/water/methanol solutions fed (%) 1st vessel | 2nd vessel | 3rd vessel | 4th vessel | 5th vessel | 6th vessel | Molar ratio NaOH/PSCl₃ | Molar ratio CH₃OH/PSCl₃ |
|---|---|---|---|---|---|---|---|---|---|---|---|---|---|---|
| 1 | −20/22.7 | −20/11.4 | −20/7.6 | −20/7.6 | −18/11.4 | −15/11.4 | 35 | 30 | 25 | 7 | 1.5 | 1.5 | 2.06 | 12.9 |
| 2 | −15/46.7 | −20/23.3 | | | | | 79.9 | 20.1 | | | | | 2.04 | 12.8 |
| 3 | −15/94.7 | −20/47.4 | −20/31.6 | −17/31.6 | −16/47.4 | −15/47.4 | 79.8 | 8.0 | 5.1 | 4.0 | 1.5 | 1.5 | 2.04 | 12.8 |
| 4 | −15/25.9 | −20/12.9 | −20/8.6 | −17/8.6 | −16/12.9 | −15/12.9 | 79.9 | 8.0 | 5.1 | 4.0 | 1.5 | 1.5 | 1.90 | 12.6 |
| 5 | −15/25.9 | −20/12.9 | −20/8.6 | −17/8.6 | −16/12.9 | −15/12.9 | 79.9 | 8.0 | 5.1 | 4.1 | 1.5 | 1.5 | 2.30 | 14.4 |
| 6 | −15/25.9 | −20/12.9 | −20/8.6 | −17/8.6 | −16/12.9 | −15/12.9 | 80.0 | 8.0 | 5.0 | 4.0 | 1.5 | 1.5 | 2.06 | 7.90 |
| 7 | −15/25.9 | −20/12.9 | −20/8.6 | −17/8.6 | −16/12.9 | −15/12.9 | 80.0 | 8.0 | 5.0 | 4.0 | 1.5 | 1.5 | 2.06 | 12.4 |
| 8 | 5/24.4 | 4/8.1 | 6/8.1 | 5/12.2 | 6/12.2 | | 79.8 | 11.6 | 5.9 | 1.3 | 1.3 | | 2.04 | 12.9 |
| 9 | 0/24.4 | 1/8.1 | 0/8.1 | 0/12.2 | 0/12.2 | | 79.8 | 11.6 | 5.9 | 1.3 | 1.3 | | 2.04 | 12.9 |
| 10 | 5/25.9 | 4/13.0 | 5/8.6 | 6/8.6 | 5/12.9 | 5/12.9 | 79.8 | 8.0 | 5.1 | 4.0 | 1.5 | 1.5 | 2.04 | 12.8 |

| Example | Concentrations of caustic soda/water/methanol solution (wt. %) NaOH | H₂O | CH₃OH | Yield (%) MMCT | Yield (%) DMCT | Yield (%) TRI | Decomposition | Remark |
|---|---|---|---|---|---|---|---|---|
| 1 | 16.51 | 0.33 | 83.16 | 1.0 | 85.0 | 7.5 | 6.5 | Concentration of caustic soda, 98.0% |
| 2 | 16.51 | 0.33 | 83.16 | 4.5 | 75.0 | 17.5 | 3.0 | Concentration of caustic soda, 98.0% |
| 3 | 13.6 | 18.1 | 68.3 | 0.5 | 83.0 | 7.0 | 9.5 | Concentration of aqueous caustic soda, 42.9% |
| 4 | 13.6 | 14.3 | 72.1 | 9.5 | 84.2 | 3.5 | 2.8 | Concentration of aqueous caustic soda, 48.7% |
| 5 | 13.6 | 18.1 | 68.3 | 0.1 | 84.7 | 12.5 | 2.7 | Concentration of aqueous caustic soda, 42.9% |
| 6 | 19.5 | 20.6 | 59.9 | 1.5 | 84.5 | 6.5 | 7.5 | Concentration of aqueous caustic soda, 48.6% |
| 7 | 11.5 | 33.0 | 55.5 | 1.0 | 79.0 | 13.3 | 6.7 | Concentration of aqueous caustic soda, 25.8% |
| 8 | 16.51 | 0.33 | 83.16 | 1.0 | 75.5 | 10.5 | 13.0 | Concentration of caustic soda, 98.0% |
| 9 | 16.51 | 0.33 | 83.16 | 1.0 | 80.0 | 9.0 | 10.0 | Concentration of caustic soda, 98.0% |
| 10 | 13.61 | 18.1 | 68.3 | 1.0 | 72.0 | 12.0 | 15.0 | Concentration of aqueous caustic soda, 42.9% |

MMCT: O—methyldichlorothiophosphate
DMCT: O,O—dimethylchlorothiophosphate
TRI: O,O,O—trimethylthiophosphate

What is claimed is:

1. A continuous process for producing O,O-di-lower-alkylchlorothiophosphate by continuously reacting phosphorus sulfochloride with a lower alcohol in the presence of caustic soda by a multi-stage reaction comprising from 3 to 8 stages in which the following conditions are satisfied:

(1) the amounts of caustic soda and a lower alcohol used are from 2 to 2.2 moles and 10 moles or more, respectively, based on 1 mole of phosphorus sulfochloride;

(2) caustic soda, water and the lower alcohol are used as a caustic soda/water/lower alcohol solution, and the caustic soda concentration of the aqueous caustic soda in said solution is from 30.0 to 99.5 wt. %;

(3) to the 1st reaction stage are continuously supplied the whole amount of phosphorus sulfochloride required and from 45 to 85 wt.% each of the amounts of caustic soda and the lower alcohol required; and to the 2nd and subsequent reaction stages are continuously supplied the residual caustic soda and lower alcohol in divided portions so that the substantial amounts supplied become successively smaller toward the final reaction stage;

(4) the temperature of the reaction system is −5° C. or lower; and
(5) the residence time in the reaction system is within 4 hours.

* * * * *